(12) United States Patent
Sugiyama et al.

(10) Patent No.: US 11,607,047 B2
(45) Date of Patent: Mar. 21, 2023

(54) SEAT DEVICE

(71) Applicant: TS TECH CO., LTD., Saitama (JP)

(72) Inventors: Shinji Sugiyama, Tochigi (JP);
Takayuki Inose, Tochigi (JP)

(73) Assignee: TS TECH CO., LTD., Saitama (JP)

( * ) Notice: Subject to any disclaimer, the term of this patent is extended or adjusted under 35 U.S.C. 154(b) by 0 days.

(21) Appl. No.: 17/225,245

(22) Filed: Apr. 8, 2021

(65) Prior Publication Data

US 2021/0227982 A1    Jul. 29, 2021

Related U.S. Application Data

(63) Continuation of application No. 16/461,833, filed as application No. PCT/JP2017/035151 on Sep. 28, 2017, now Pat. No. 10,973,334.

(30) Foreign Application Priority Data

Nov. 18, 2016    (JP) .............................. JP2016-225357

(51) Int. Cl.
*A47C 7/62*    (2006.01)
*B60N 2/90*    (2018.01)
(Continued)

(52) U.S. Cl.
CPC .............. *A47C 7/62* (2013.01); *A61B 5/1123* (2013.01); *A61B 5/18* (2013.01); *A61B 5/4806* (2013.01);
(Continued)

(58) Field of Classification Search
CPC .......... A47C 1/023; A47C 1/024; A47C 3/026
See application file for complete search history.

(56) References Cited

U.S. PATENT DOCUMENTS 4,136,685 A  *  1/1979  Ramey ............... A61H 23/0263
                                                              5/915
5,909,924 A      6/1999  Roslund
                          (Continued)

FOREIGN PATENT DOCUMENTS

JP    2011-254882 A    12/2011
JP    2014-167927 A     9/2014
             (Continued)

OTHER PUBLICATIONS

International Search Report dated Dec. 5, 2017 for the corresponding international application No. PCT/JP2017/035151, with English translation.

*Primary Examiner* — Syed A Islam
(74) *Attorney, Agent, or Firm* — Michael Best & Friedrich LLP

(57) ABSTRACT

In a configuration in which a holder holding a controller is mounted on a seat part with a plate-shaped member, the exposure of the mounting part of the plate-shaped member on which the holder is mounted is eliminated. A seat device includes a pressure sensor measuring a value relating to the seated person's state, a vibration imparting device a vibration imparting operation, an ECU controlling the vibration imparting device corresponding to the measurement result of the pressure sensor, a holder holding the ECU, and a mounting bracket fixed to a lower frame such that the holder is mounted on the lower frame of a seat part. The mounting bracket includes a mounting projection on which a side wall of the holder is mounted in a predetermined mounting direction. When the side wall is mounted on the mounting projection, the mounting projection is covered with the side wall.

13 Claims, 14 Drawing Sheets

(51) Int. Cl.
*A61B 5/11* (2006.01)
*A61B 5/18* (2006.01)
*A61B 5/00* (2006.01)
*A61M 21/00* (2006.01)

(52) U.S. Cl.
CPC .............. *A61M 21/00* (2013.01); *B60N 2/90* (2018.02); *A61M 2021/0022* (2013.01); *A61M 2205/10* (2013.01); *A61M 2205/3331* (2013.01); *A61M 2209/082* (2013.01); *B60N 2002/981* (2018.02)

(56) References Cited

U.S. PATENT DOCUMENTS

| | | | | |
|---|---|---|---|---|
| 6,139,103 | A * | 10/2000 | Hybarger | A47C 3/30 297/300.5 |
| 6,588,843 | B1 | 7/2003 | Ebenstein | |
| 6,682,494 | B1 * | 1/2004 | Sleichter, III | B60N 2/976 297/217.3 |
| 2011/0074197 | A1 * | 3/2011 | Okamoto | A47C 1/03294 297/340 |
| 2018/0118071 | A1 | 5/2018 | Sugiyama | |

FOREIGN PATENT DOCUMENTS

| | | | | |
|---|---|---|---|---|
| JP | 2016-185256 | A | 10/2016 | |
| JP | 2016-193038 | A | 11/2016 | |
| JP | 6600964 | B2 * | 11/2019 | ............. H04L 12/12 |
| JP | 6600965 | B2 | 11/2019 | |

* cited by examiner

SEAT DEVICE

CROSS-REFERENCE TO RELATED APPLICATIONS

This application is a continuation of U.S. patent application Ser. No. 16/461,833, filed on May 17, 2019, which, in turn, is a National Stage Entry of PCT Application Serial Number PCT/JP2017/035151, filed Sep. 28, 2017. Further, this application claims priority from Japanese Patent Application Serial Number JP 2016-225357, filed Nov. 18, 2016, the entire contents of which are hereby incorporated by reference into this application.

TECHNICAL FIELD

The present invention relates to a seat device, and particularly to a seat device having a seat part, a sensor, a moving device, and a control mechanism.

BACKGROUND ART

Among seat devices having a chair or a seat part, such as a seat, there are some seat devices mounted with a sensor that senses the state of a seated person seated on the seat part (e.g. the wakefulness level). There are also seat devices including a device (a moving device) that performs a predetermined operation suitable for the state of a seated person. In such seat devices, a control mechanism is usually provided. The control mechanism controls the moving device corresponding to the measurement result of the above-described sensor.

In the seat device including the above-described control mechanism, the control mechanism is sometimes mounted at a predetermined position in the seat part. In specific description taking an example, in a chair of Patent Literature 1, an ECU (Electrical Control Unit) that is a control mechanism is held on a holder. The chair described in Patent Literature 1 is configured in which the holder holding the ECU is screwed on the under surface of the seat part and hence the ECU is mounted on the seat part through the holder.

CITATION LIST

Patent Literature

PATENT LITERATURE 1: JP 2016-185256

SUMMARY OF INVENTION

Technical Problem

As a method of mounting a control mechanism on a seat part through a holder, a method can be thought with which a plate-shaped member, such as a bracket, is fixed to a seat part and a holder holding the control mechanism is mounted on a predetermined part (a mounting part) of the plate-shaped member. In the case in which such a configuration is adopted, from the viewpoint of ensuring the quality of the seat device, the importance is to minimize the exposure of the mounting part of the plate-shaped member on which the holder is mounted.

In the case in which the control mechanism is mounted on the seat part using the above-described plate-shaped member, desirably, the holder holding the control mechanism is easily mounted on the plate-shaped member.

Therefore, the present invention is made in view of the problems. An object is to provide a seat device that can eliminate the exposure of the mounting part of a plate-shaped member on which a holder is mounted in the configuration in which the holder holding a control mechanism is mounted on a seat part with the plate-shaped member.

Another object of the present invention is to more easily mount a holder holding a control mechanism in mounting the holder on a seat part with a plate-shaped member.

Solution to Problem

The problems are solved by a seat device according to the present invention, the seat device including a seat part on which a seated person is seated, a sensor configured to measure a measurement value relating to a state of the seated person seated on the seat part, a moving device having a moving part, the moving device being configured to perform an operation of moving the moving part, a control mechanism configured to control the operation of the moving device corresponding to a measurement result of the sensor, a holder holding the control mechanism, and a plate-shaped member fixed to the seat part such that the holder is mounted on the seat part. The plate-shaped member includes a mounting part on which a mounted part of the holder is mounted in a predetermined mounting direction. In a state in which the mounted part is mounted on the mounting part, the mounting part is covered with the mounted part in the mounting direction.

In the seat device according to the present invention thus configured, in mounting the holder holding the control mechanism on the seat part using the plate-shaped member, the mounted part of the holder is mounted on the mounting part of the plate-shaped member in a predetermined mounting direction. In the state in which the mounted part is mounted on the mounting part, the mounting part is covered with the mounted part in the mounting direction. That is, in the state in which the control mechanism is mounted on the seat part, the exposure of the mounting part of the plate-shaped member is eliminated by the holder (strictly speaking, the mounted part).

In the above-described seat device, the mounting part may have a first mounting part and a second mounting part formed at positions apart from each other in the mounting direction. The plate-shaped member may have a plate-shaped member fixing part formed such that the plate-shaped member is fixed to the seat part. The plate-shaped member fixing part may be formed between the first mounting part and the second mounting part in the mounting direction.

In the above-described configuration, the plate-shaped member fixing part is formed between the first mounting part and the second mounting part of the plate-shaped member. In other words, the first mounting part and the second mounting part are provided on the outer side of the plate-shaped member fixing part in the mounting direction. With such a configuration, the situations are easily avoided in which problems are caused on the work that mounts the mounted part of the holder on the mounting parts due to fixing the plate-shaped member to the seat part at the plate-shaped member fixing part.

In the above-described seat device, a lower portion of the seat part may have a frame. The plate-shaped member may have an engaging part engaged with an edge portion of the frame with the plate-shaped member fixed to the seat part.

The engaging part may be engaged with the edge portion of the frame in an engaging direction intersecting with the mounting direction.

In the above-described configuration, the plate-shaped member has the engaging part, and the above-described engaging part is engaged with the edge portion of the frame of the seat part with the plate-shaped member fixed to the seat part. With such a configuration, the plate-shaped member can be fixed to the frame while the attitude of the plate-shaped member is stabilized.

In the above-described seat device, the engaging part may have a first engaging part and a second engaging part formed at positions apart from each other in the mounting direction. The plate-shaped member may have a contact part in contact with an under surface of the frame with the plate-shaped member fixed to the seat part. The contact part may have a first contact part and a second contact part formed at positions apart from each other in the mounting direction. A first joining rib extending so as to join the first engaging part to the first contact part and a second joining rib extending so as to join the second engaging part to the second contact part may be provided on the plate-shaped member.

In the above-described configuration, the engaging part of the plate-shaped member has the first engaging part and the second engaging part. The plate-shaped member has the first contact part and the second contact part as the contact parts that are in contact with the under surface of the frame with the plate-shaped member fixed to the seat part. The first joining rib joining the first engaging part to the first contact part and the second joining rib joining the second engaging part to the second contact part are provided on the plate-shaped member. With such a configuration, the rigidity of the engaging parts and the contact parts can be improved. Thus, the engaging parts appropriately keep the engaging state with the edge portion of the frame of the seat part. The contact parts appropriately keep the state in contact with the under surface of the frame.

In the above-described seat device, a front end portion of the seat part may have a portion overhanging downward. In the front end portion of the seat part, the portion overhanging downward may be located on a front side of a front end of the holder, and the portion overhanging downward may cover at least apart of the front end of the holder in a front to back direction of the seat part.

In the above-described configuration, the front end portion of the seat part has the portion overhanging downward, and the portion covers a part of the front end of the holder. That is, according to the above-described configuration, the front end of the holder can be protected using a part of the front end portion of the seat part.

In the above-described seat device, the mounting direction may be a direction along a front to back direction of the seat part or along a width direction of the seat part. The mounting part may protrude along a vertical direction of the seat part with the plate-shaped member fixed to the seat part.

In the above-described configuration, in the plate-shaped member, the mounting part protrudes along the vertical direction of the seat part. In mounting the mounted part of the holder on the mounting part of the plate-shaped member, the mounted part of the holder is mounted along the front to back direction of the seat part or along the width direction of the seat part. With such a configuration, the mounted part can be more easily mounted compared with the configuration in which the mounted part is mounted on the mounting part along the vertical direction of the seat part.

In the above-described seat device, a battery configured to supply electric power to the moving device may be included. The holder may hold the moving device and the battery together with the control mechanism.

In the above-described configuration, the holder holding the control mechanism also serves as a member holding the moving device and the battery. With such a configuration, the number of components (the number of the holders) can be made much smaller compared with the configuration in which the holders are provided individually to the control mechanism, the moving device, and the battery.

Advantageous Effects of Invention

According to the seat device of the present invention, in the state in which the holder holding the control mechanism is mounted on the seat part using the plate-shaped member, the exposure of the mounting part of the plate-shaped member can be eliminated by the holder.

According to the seat device of the present invention, the situations are easily avoided in which problems are caused on the work that mounts the mounted part of the holder on the mounting part due to fixing the plate-shaped member to the seat part at the plate-shaped member fixing part.

According to the seat device of the present invention, the plate-shaped member can be fixed to the frame while the attitude of the plate-shaped member is stabilized.

According to the seat device of the present invention, the rigidity of the engaging part and the contact part can be improved. Thus, the engaging part appropriately keeps the engaging state with the edge portion of the frame of the seat part, and the contact part appropriately keeps the contact state with the under surface of the frame.

According to the seat device of the present invention, the front end of the holder can be protected using a part of the front end portion of the seat part.

According to the seat device of the present invention, in mounting the mounted part of the holder on the mounting part of the plate-shaped member, the mounted part is mounted along the front to back direction of the seat part or along the width direction of the seat part. Thus, the mounted part can be more easily mounted compared with the configuration in which the mounted part is mounted on the mounting part along the vertical direction of the seat part.

In the seat device according to the present invention, the holder holding the control mechanism also serves as a member holding the moving device and the battery. Thus, the number of components (the number of the holders) is made much smaller compared with the configuration in which the holders are provided individually to the control mechanism, the moving device, and the battery.

DESCRIPTION OF EMBODIMENTS

In the following, a seat device according to an embodiment (the present embodiment) of the present invention will be described. The seat device according to the embodiment is configured in which a sensor that measures measurement values changing corresponding to the wakefulness level of a seated person, a device that operates corresponding to the measurement result of the sensor and equipment relating to the device are installed on a typical chair or a seat. According to the seat device of the embodiment, when the wakefulness level of the seated person is lowered, a change in the wakefulness level is sensed, the above-described device is operated corresponding to the wakefulness level, and then an appropriate stimulus is imparted to the seated person. Thus, the wakefulness level of the seated person can be improved (restored).

In the following, a seat device configured in which the above-described sensor or device, for example, is installed on a typical office chair is taken as an example, and the configuration of the seat device will be described. Note that the embodiment described below is merely an example. Instead of the office chair, a seat device may be configured using conveyance seats used for conveyances, such as vehicles, ships, or air crafts, or using seats placed in buildings, such as facilities.

Note that in the following description, the positions, attitudes, and orientations of the component members of the seat device are the positions, attitudes, and orientations where the seat device is in a normal state (specifically, the seat surface is on the top side and the lower ends of legs are in contact with the floor surface) unless otherwise specified.

Figure 1:
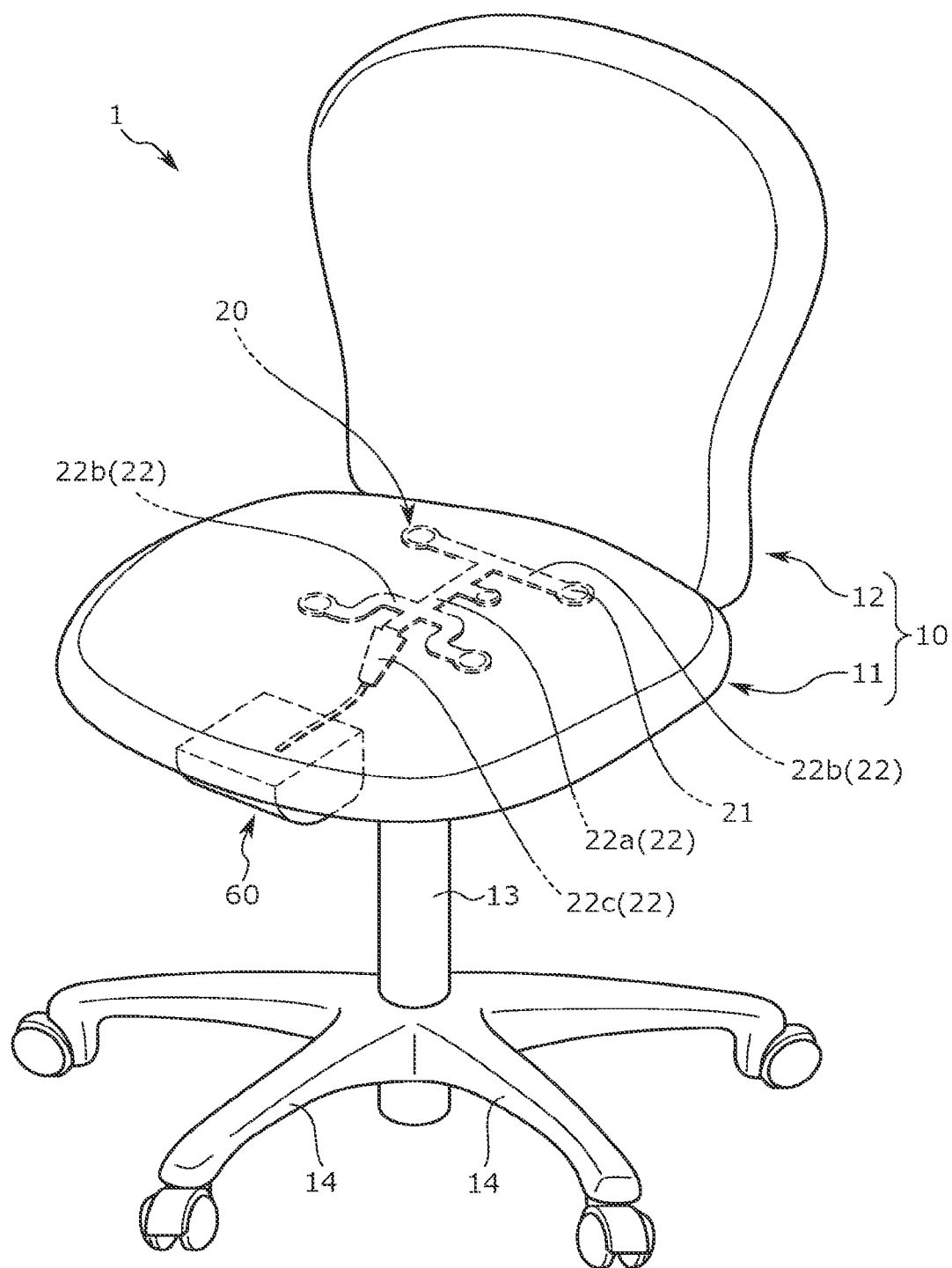
FIG. 1 is a perspective view showing the outside of a seat device according to an embodiment of the present invention.
Figure 2A:
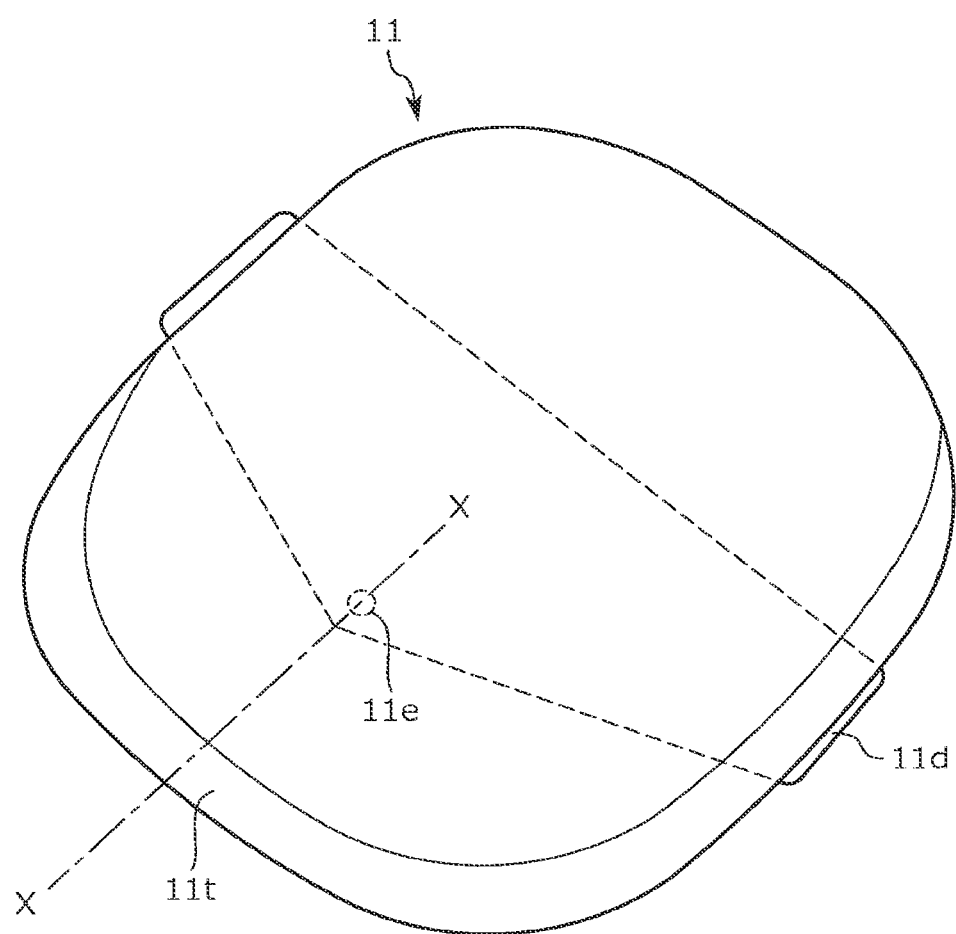
FIG. 2A is an outside view of a seat part.
Figure 2B:
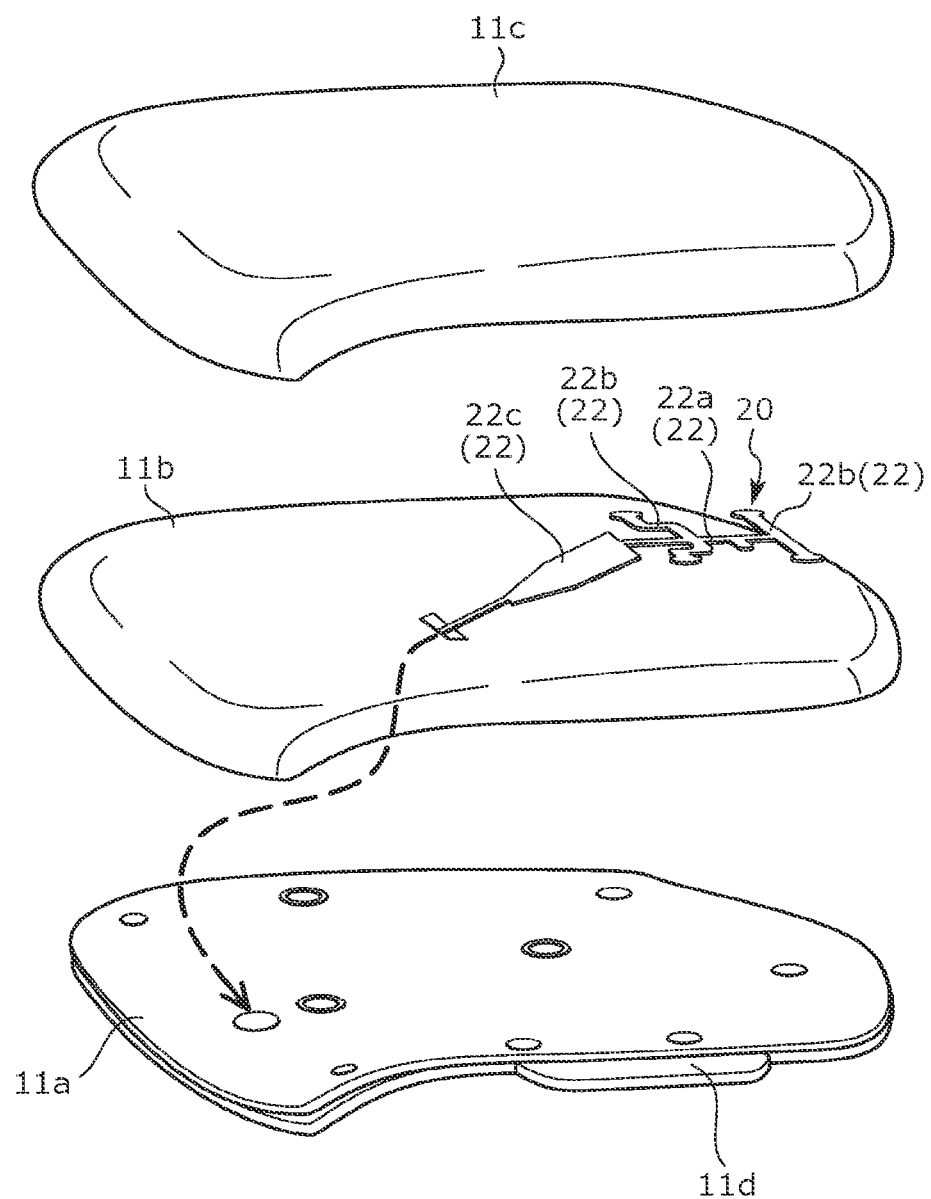
FIG. 2B is an illustration of the configuration of the seat part.
Figure 3:
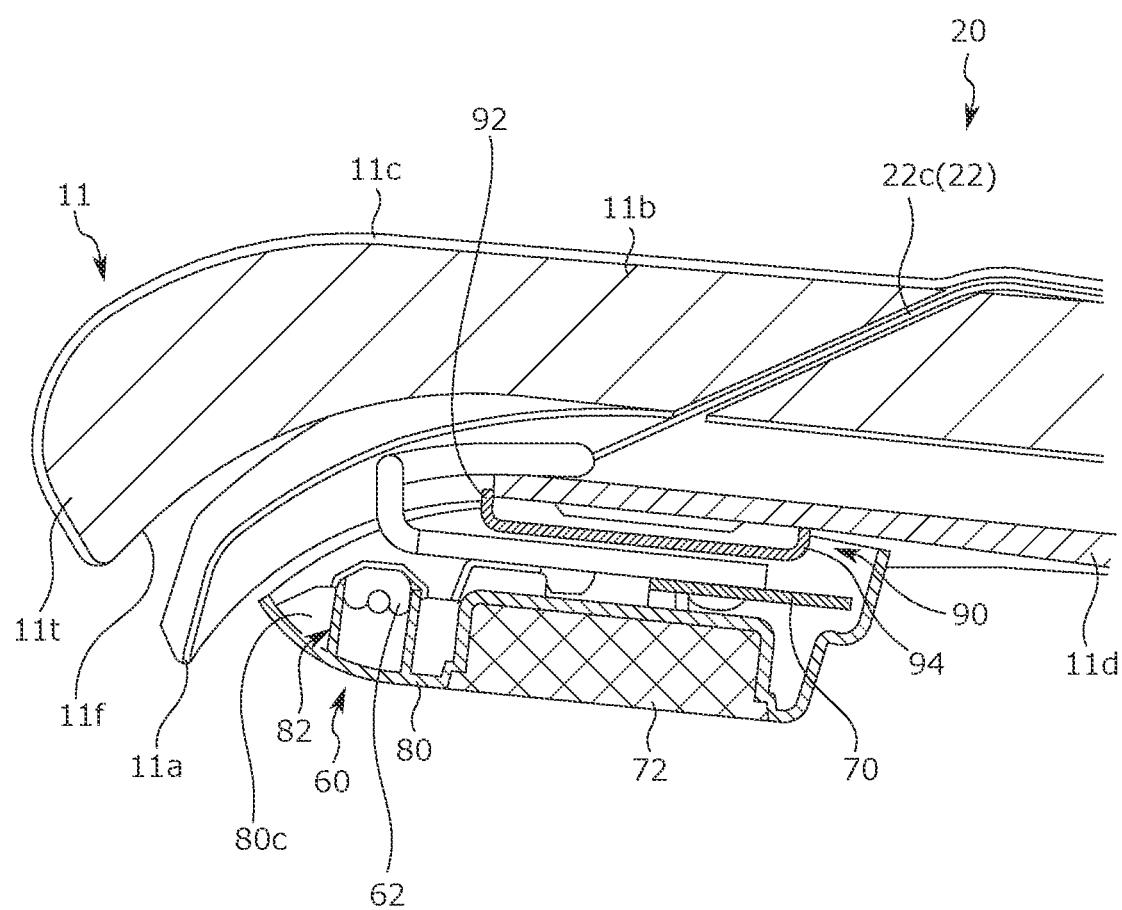
FIG. 3 is a side cross-sectional view showing positions at which devices around the seat part are disposed.
Figure 4:
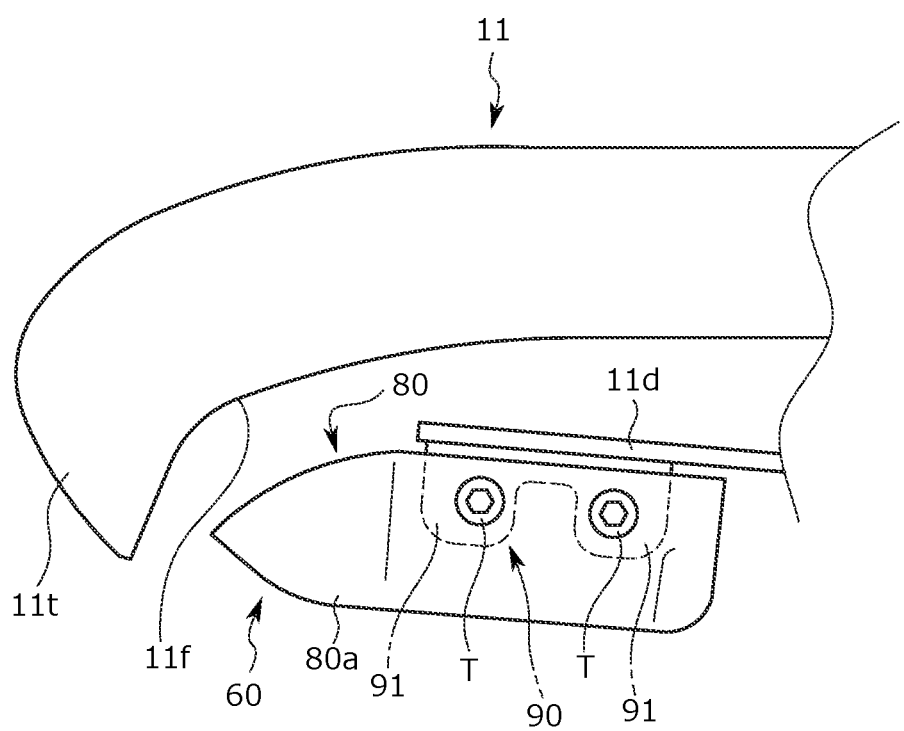
FIG. 4 is a view of the front end portion of the seat part when viewed from the lateral side.

As shown in FIG. 1, the seat device according to the embodiment (in the following, a seat device 1) has a chair main body 10 and a respiration sensor unit 20. First, referring to FIGS. 1 to 4, the configurations of the chair main body 10 and the respiration sensor unit 20 will be described. FIG. 1 is a perspective view showing the outside of the seat device 1 according to the embodiment. FIG. 2A is an outside view of a seat part 11 in the chair main body 10. FIG. 2B is an illustration of the configuration of the seat part 11, which is an explored view of the components of the seat part 11. FIG. 3 is a side cross-sectional view showing the position at which the respiration sensor unit 20 is disposed in the seat part 11, which is a view showing a cross section along line X-X in FIG. 2A. FIG. 4 is a view of the front end portion of the seat part 11 when viewed from the lateral side.

The chair main body 10 is the part of the seat device 1 except the respiration sensor unit 20 and an awakening unit 60, described later, having a structure similar to a publicly known office chair. That is, as shown in FIG. 1, the chair main body 10 has the seat part 11 on which a seated person is seated and a backrest portion 12 on which a seated person's back reclines. The seat part 11 has the outside shown in FIG. 2A, and supports seated person's buttocks on the top surface. The seat part 11 is supported by a support post 13 disposed at the position below the seat part 11. At the lower portion of the support post 13, leg parts 14 are provided at every 60 degrees or 90 degrees about the support post 13. At the tip end portions of the leg parts 14, a caster is mounted. In the state in which the casters are in contact with the floor surface, the seated person sits on the top surface (i.e., the seat surface) of the seat part 11.

In the description of the configuration of the seat part 11 with reference to FIG. 2B, the seat part 11 is configured in which a pad material 11b is placed on a resin frame 11a and this pad material 11b is covered with a skin material 11c. The resin frame 11a has a size enough to support the pad material 11b from below.

In the lower portion of the resin frame 11a, a lower frame 11d is disposed. The lower frame 11d is a resin frame that constitutes the lower portion of the seat part 11, supporting the resin frame 11a from below. The lower frame 11d is shaped in an oblong pentagonal shape (more strictly speaking, a home base shape) wide in the width direction of the seat part 11 having a nearly triangular front end portion.

As shown in FIG. 3, the front end portions of the resin frame 11a, the pad material 11b, and the skin material 11c are curved downward as the front end portions come close to the front end. In other words, the front end portion of the seat part 11 has a portion overhanging downward (in the following, an overhang portion 11t).

The respiration sensor unit 20 is a device that measures measurement values relating to the state of the seated person seated on the seat part 11, and more specifically to measurement values changing corresponding to the wakefulness level (sleepiness) of the seated person. As shown in FIG. 1, the respiration sensor unit 20 has pressure sensors 21, conductor wires (not shown) forming the transmission lines of signals outputted from the pressure sensors 21, and a conductor wire holding film 22 to which the conductor wires are adhered.

The pressure sensor 21 is formed of a publicly known pressure sensor. A plurality of pressure sensors 21 is disposed in the seat part 11, and the pressure sensor 21 measures a pressure (a seating pressure) applied to the seat surface when the seated person is seated on the seat part 11. Here, the seating pressure is a value that periodically changes corresponding to the physiological activities of the seated person, specifically to respiration, and is a measurement value measured at the pressure sensor 21. The seating pressures measured at the pressure sensors 21 change reflecting the wakefulness level of the seated person. In other words, the pressure sensors 21 are sensors that measure the seating pressures changing corresponding to the wakefulness level of the seated person. The pressure sensors 21 output signals corresponding to measurement results.

Note that in the embodiment, the pressure sensors 21 are disposed in the seat part 11 being sandwiched between the pad material 11b and the skin material 11c near the location where the seated person's buttocks are placed. The pressure sensors 21 are disposed being distributed in the front to back direction and the width direction of the seat part 11.

The conductor wires form the transmission lines of signals outputted from the pressure sensors 21. The conductor wire is provided on each of the pressure sensors 21. The conductor wire holding film 22 has a two-layer structure having a front layer and a back layer, and sandwiches and holds the pressure sensors 21 and the conductor wires between the layers. Note that the conductor wire holding film 22 is formed of a material having electrical conductivity, and made of polyethylene naphthalate, for example. The conductor wire holding film 22 has the thickness and flexibility to the extent that the conductor wire holding film 22 can be easily deformed.

The conductor wire holding film 22 has a portion extending along the front to back direction of the seat part 11 (in the following, a main portion 22a) and a portion extending from the main portion 22a to the position at which the pressure sensor 21 is disposed (in the following, a branch portion 22b). In the midway portion of the main portion 22a, a wide-width portion 22c in width wider than the width of the other portions is provided. The front end portion of this wide-width portion 22c has a tapered shape having the width tapered toward the front side.

The terminations of the conductor wires held on the conductor wire holding film 22 are connected to an ECU 70 (the ECU 70 will be described later) provided below the seat part 11. In other words, the conductor wires and the conductor wire holding film 22 are disposed so as to penetrate the seat part 11 from the top surface of the pad material 11b to below the seat part 11. In more specific description, the resin frame 11a and the pad material 11b are formed with a through hole. The conductor wires and the conductor wire holding film 22 are passed through this through hole, and thus disposed from the top surface of the pad material 11b toward below the seat part 11.

Note that the through hole formed on the pad material 11b is inclined toward the vertical direction of the seat part 11 (in other words, the thickness direction of the pad material 11b). Specifically, the through hole is inclined toward the front side. In the through hole, the wide-width portion 22c of the main portion 22a of the conductor wire holding film 22 is disposed. Here, the through hole formed on the pad material 11b as described above is inclined toward the vertical direction of the seat part 11, and hence this further increases the entire length of the through hole. Consequently, the wide-width portion 22c can be entirely housed in the through hole.

Figure 5:
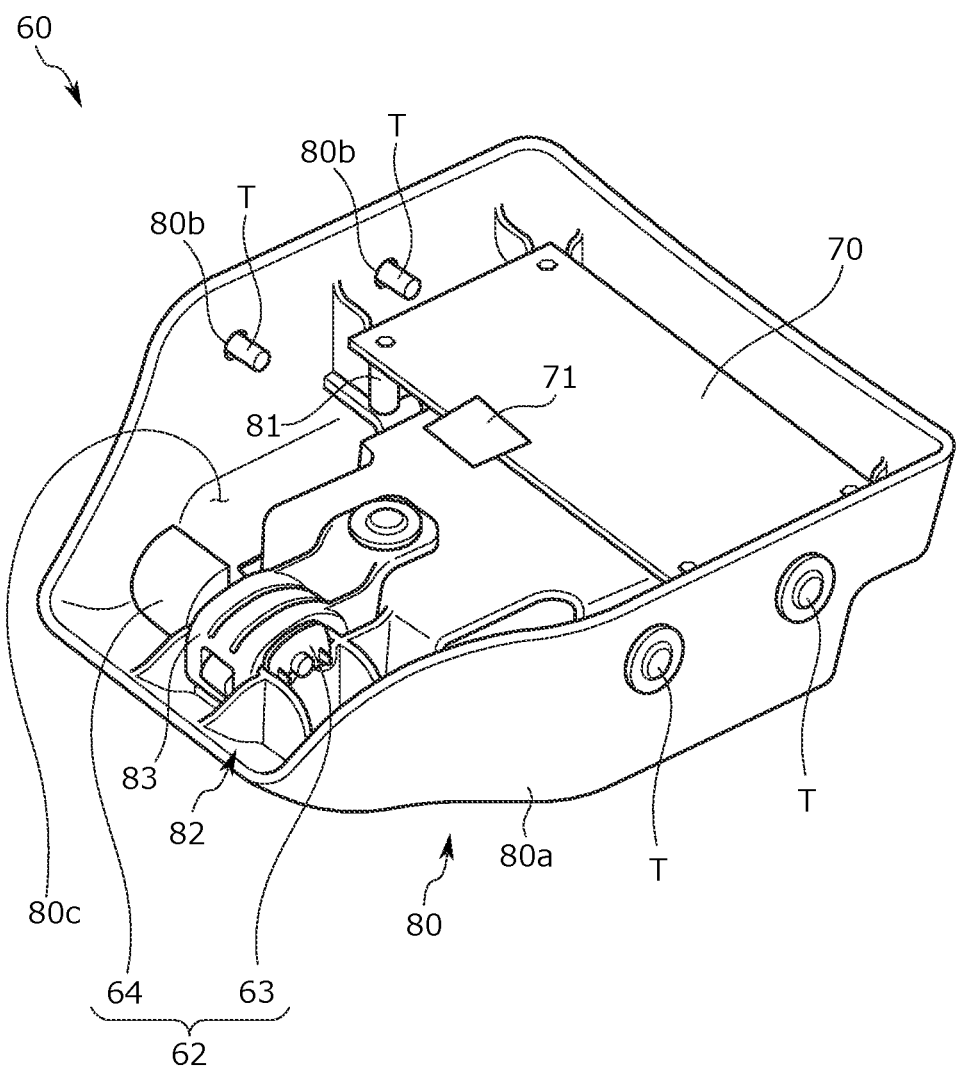
FIG. 5 is a view of a holder holding a control mechanism when viewed from above.
Figure 6:
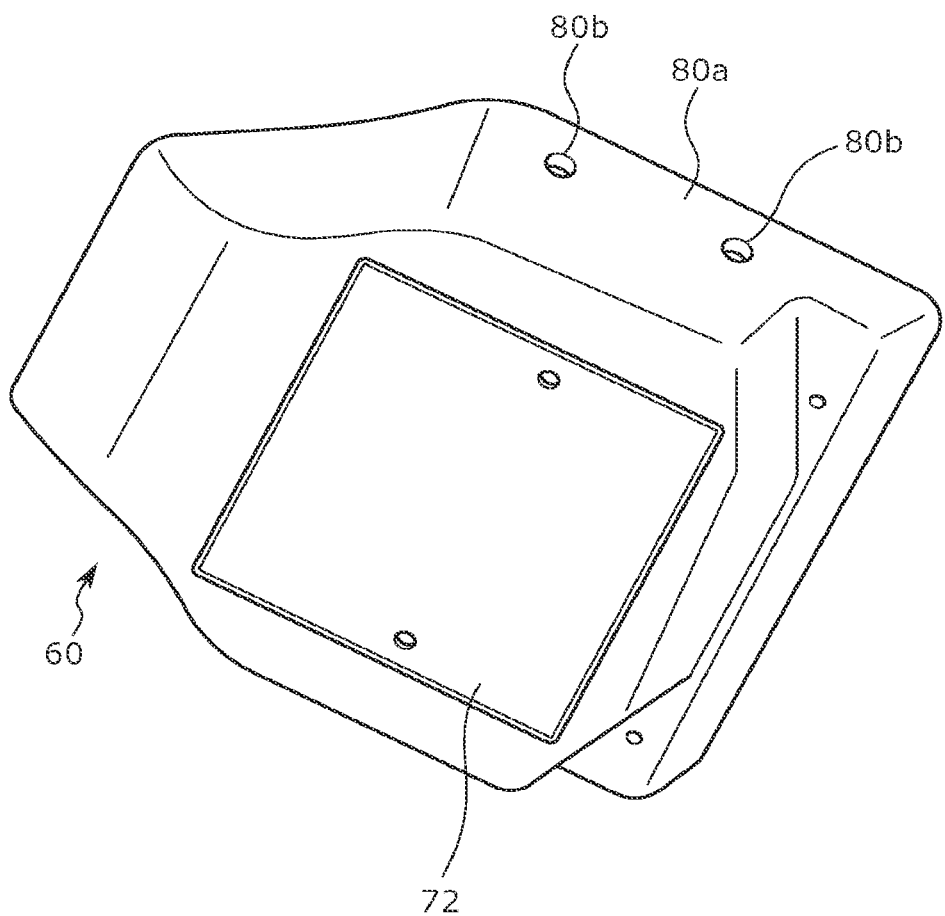
FIG. 6 is a view of the holder holding a battery when viewed from below.
Figure 7:
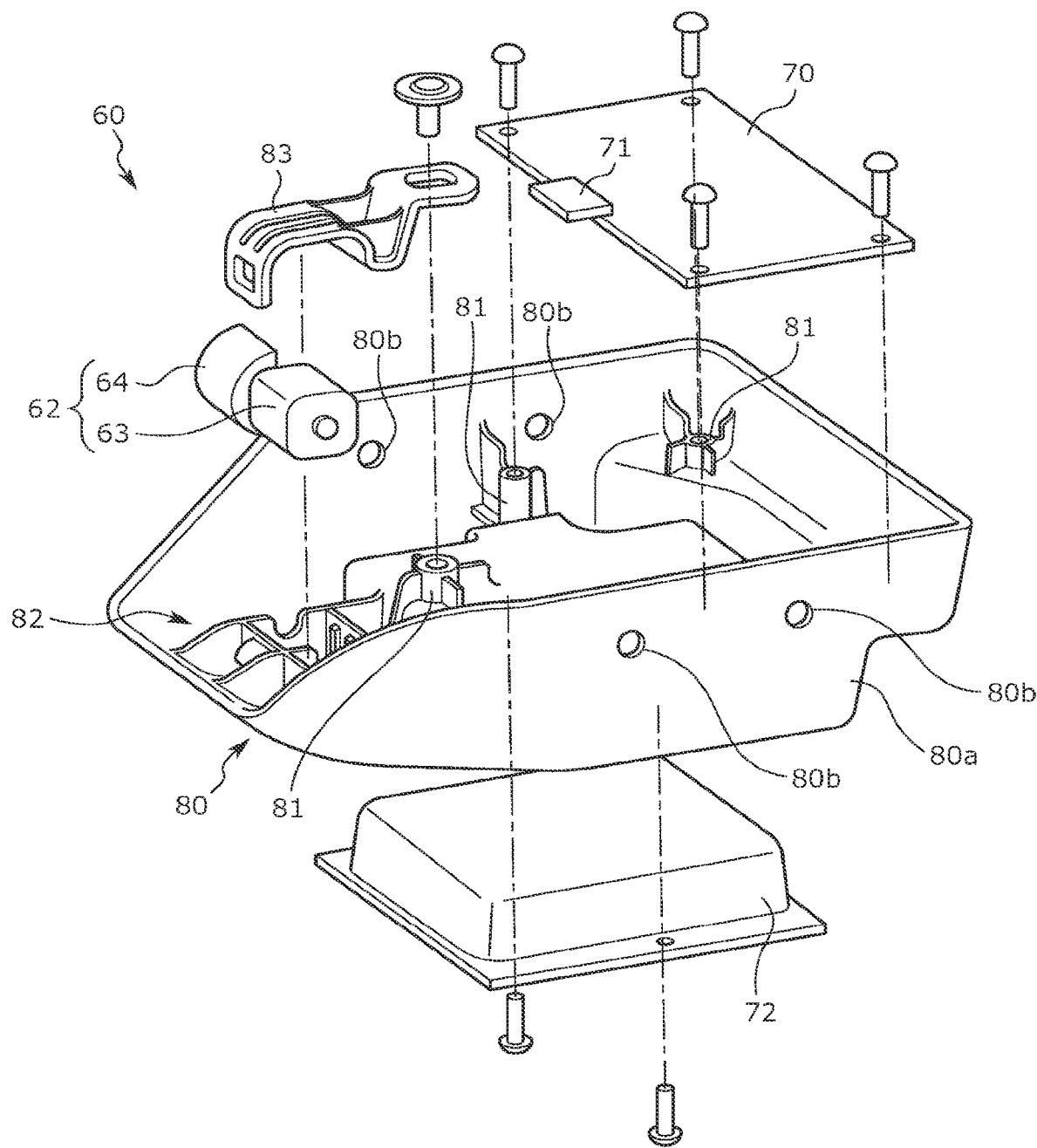
FIG. 7 is a view relating to a method of holding the control mechanism, a moving device, and the battery on the holder.

The configuration of the seat device 1 is again described. The seat device 1 has the awakening unit 60 shown in FIG. 5 and other drawings. In the following, referring to FIGS. 5 to 7, the configuration of the awakening unit 60 will be described. FIG. 5 is a view of the awakening unit 60 when viewed from above. FIG. 6 is a view of the awakening unit 60 when viewed from below. FIG. 7 is an assembly diagram of the awakening unit 60.

The awakening unit 60 has the outside shown in FIG. 5, and is mounted below the seat part 11. The awakening unit 60 is a mechanism that improves the wakefulness level of the seated person by imparting vibrations as a physical stimulus to the seated person. The specific configuration of the awakening unit 60 will be described. As shown in FIGS. 5, 6, and 7, the awakening unit 60 has a vibration imparting device 62, the ECU 70, a battery 72, and a holder 80.

The vibration imparting device 62 corresponds to a moving device, and performs a vibration imparting operation in order to improve the wakefulness level of the seated person. The vibration imparting device 62 is formed of an unbalance mass type motor. As shown in FIG. 7, the vibration imparting device 62 is composed of a motor 63 and a semi-columnar rotor 64 mounted on the rotating shaft of the motor 63. The rotor 64 corresponds to a moving part. The vibration imparting device 62 performs the vibration imparting operation as the operation of moving the rotor 64, and imparts a vibration stimulus to the seated person. In specific description, the motor 63 is activated to rotate the rotor 64, and hence periodical vibrations of the seat part 11 are generated. These vibrations are transmitted to the seat part 11 through the holder 80 and a mounting bracket 90, described later, and finally reached on the seated person seated on the seat part 11.

The ECU 70 corresponds to a control mechanism, and controls the vibration imparting device 62. In more specific description, the ECU 70 is formed of a control substrate, and connected to the termination portions of the conductor wires extending from the pressure sensors 21 through a termination terminal 71. The ECU 70 receives a signal (i.e., the measurement result of the seating pressure) outputted from the pressure sensor 21, and performs the process of operating the present wakefulness level of the seated person based on the signal. The ECU 70 controls the vibration imparting device 62 such that vibrations are generated at strength and a frequency corresponding to the operated wakefulness level. In other words, the ECU 70 controls the vibration imparting device 62 corresponding to the measurement result of the pressure sensor 21.

In this connection, as a method of determining the wakefulness level of the seated person based on the measurement result of the seating pressure, a publicly known determination method can be used. For example, a waveform showing a periodic change in the seating pressure is identified from the measurement result of the pressure sensor 21, and the wakefulness level of the seated person can be determined from the length of the period of the waveform (for easy understanding, intervals at which peaks appear in the waveform).

Note that as shown in FIG. 5, the termination terminal 71 is provided on the front end portion of the ECU 70. In other words, the termination portions of the conductor wires extending from the pressure sensors 21 are drawn from the front side of the ECU 70 toward the ECU 70, and connected to the termination terminal 71.

The battery 72 is a device that supplies electric power to the vibration imparting device 62 and the ECU 70. Note that as shown in FIG. 7, the battery 72 according to the embodiment has an outside shape in a nearly rectangular cuboid. The holder 80 is a container (a case) that holds the vibration imparting device 62, the ECU 70, and the battery 72, and has an outside shown in FIG. 7. In the following, the configuration of the holder 80 will be described in detail.

The holder 80 is a resin container shaped in a nearly boat shape, and has an opening on its top end. This opening reaches the front end upper portion of the holder 80. On the lower portion of the bottom wall of the holder 80, a battery housing space (not shown) is provided. The battery housing space is formed in a hollow on the under surface of the bottom wall in a nearly rectangular cuboid shape. The battery 72 is fit into this battery housing space, and the battery 72 is fixed to the bottom wall of the holder 80 with screws, for example. Thus, as shown in FIG. 6, the battery 72 is held on the bottom wall of the holder 80.

The holder 80 has a side wall 80a around the bottom wall. This side wall 80a is provided so as to surround the bottom wall of the holder 80. As shown in FIG. 7, the vibration imparting device 62 and the ECU 70 are held (housed) in the space surrounded by the side wall 80a and the bottom wall of the holder 80 (in the following, the internal space of the holder 80). In specific description, in the region located on the rear side of the internal space of the holder 80, a plurality of bosses 81 is provided. The boss 81 is provided in order to screw the ECU 70. Four bosses 81 are provided at positions corresponding to the corner portions of the control substrate in a nearly rectangular shape forming the ECU 70. As shown in FIG. 7, the ECU 70 is housed in the rear part of the internal space of the holder 80, a screw is inserted into each of screw holes formed at the corner portions of the ECU 70, and the screw is fastened to the boss 81. Thus, the ECU 70 is held on the holder 80 being housed in the internal space of the holder 80.

Note that as shown in FIG. 5, in the internal space of the holder 80, the ECU 70 is held above the portion protruding in a nearly rectangular cuboid shape that forms the above-described battery housing space in the bottom wall of the holder 80.

In the internal space of the holder 80, a motor holding part 82 is provided on the region located on the front side. This motor holding part 82 has a pair of vertical walls erected from the bottom wall and a pair of orthogonal walls provided orthogonal to the vertical walls. The motor 63 of the vibration imparting device 62 is fit into the lattice shaped space surrounded by the vertical walls and the orthogonal walls. After that, with the outer surface of the motor 63, a presser plate 83 shown in FIG. 7 is engaged. The presser plate 83 is fixed to a predetermined portion of the holder 80 (strictly speaking, the portion protruding in a nearly rectangular cuboid shape that forms the above-described battery housing space in the bottom wall of the holder 80). Thus, the vibration imparting device 62 is held on the motor holding part 82 with the vibration imparting device 62 including the motor 63 pressed against the motor holding part 82 by the presser plate 83.

As described above, the holder 80 is configured to hold the vibration imparting device 62, the ECU 70, and the battery 72. Thus, in the embodiment, the number of components (the number of the holders) is much smaller compared with the configuration in which the holders are provided individually to the above three devices.

As shown in FIGS. 3 and 4, the awakening unit 60 described so far is mounted at the position below the front end portion of the seat part 11. In more specific description, the holder 80 holding the vibration imparting device 62, the ECU 70, and the battery 72 is mounted on the lower frame 11*d* of the seat part 11 through the mounting bracket 90. Thus, the awakening unit 60 is disposed at the position below the front end portion of the seat part 11.

Figure 8:
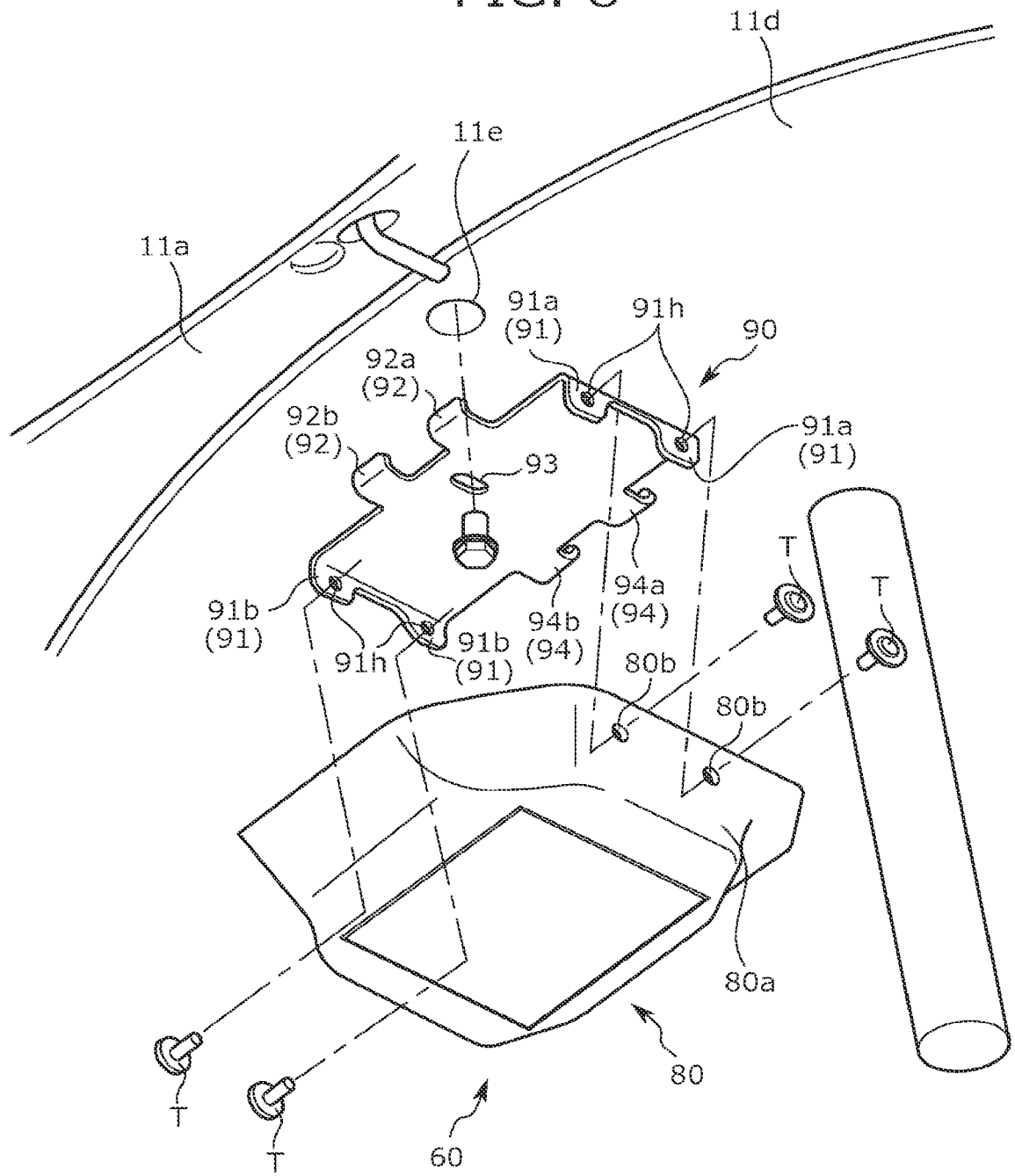
FIG. 8 is a view relating to a method of mounting the holder on the frame of the seat part using a plate-shaped member.
Figure 9A:
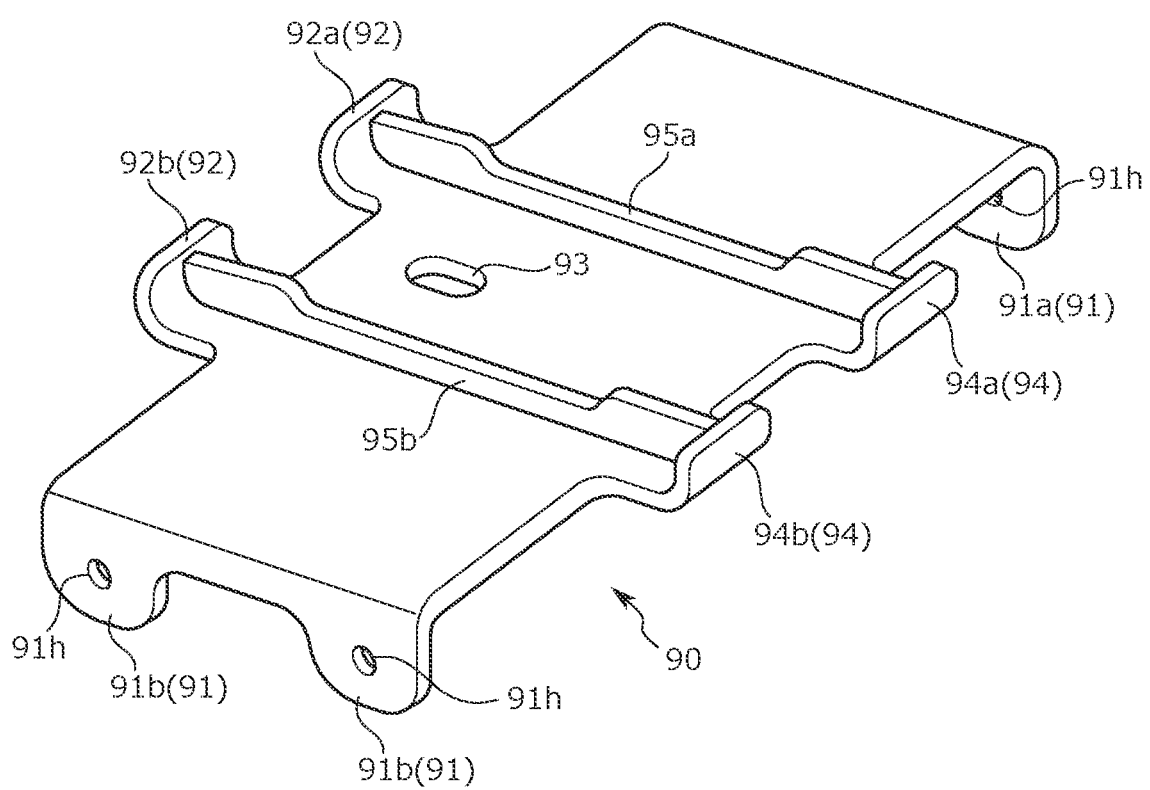
FIG. 9A is a perspective view of the plate-shaped member.
Figure 9B:
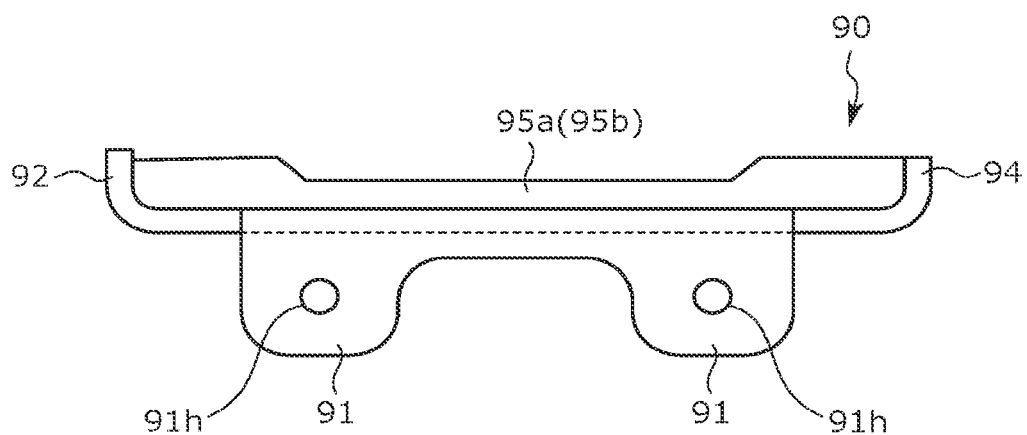
FIG. 9B is a front view of the plate-shaped member.
Figure 10:
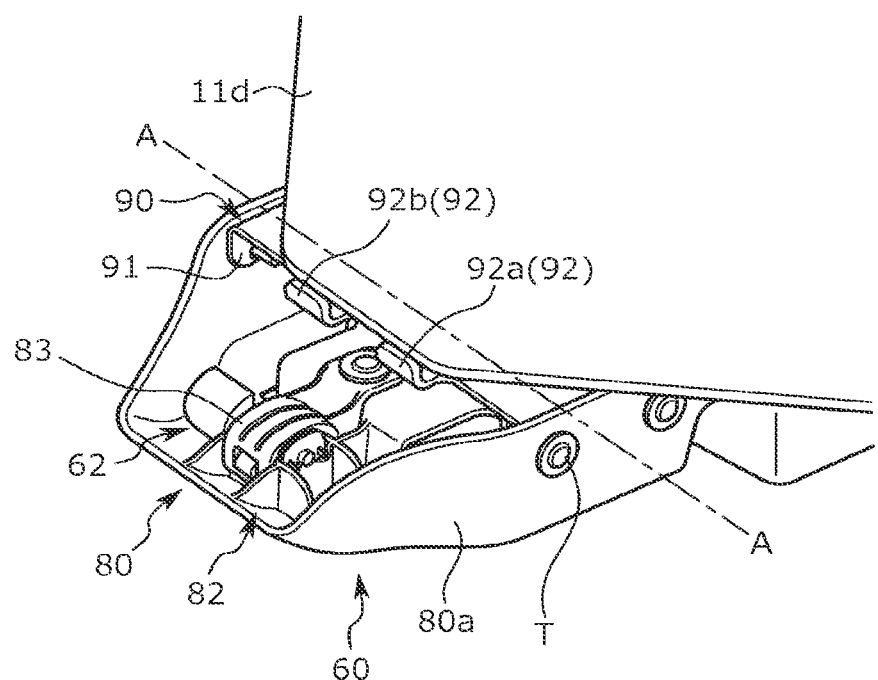
FIG. 10 is a view of the holder mounted on the frame of the seat part when viewed from above.
Figure 11:
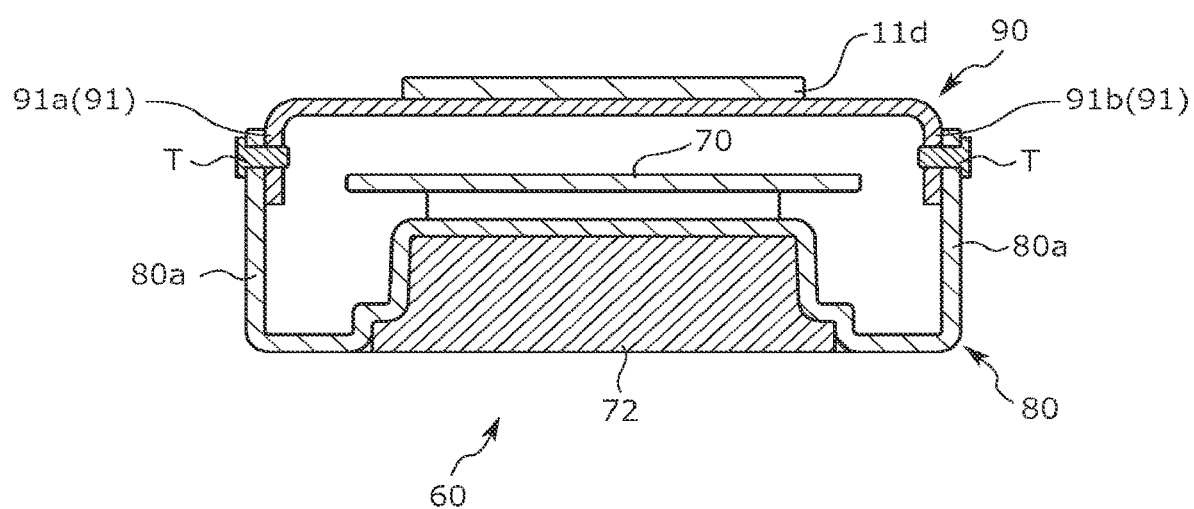
FIG. 11 is a cross-sectional view taken along line A-A in FIG. 10.
Figure 12:
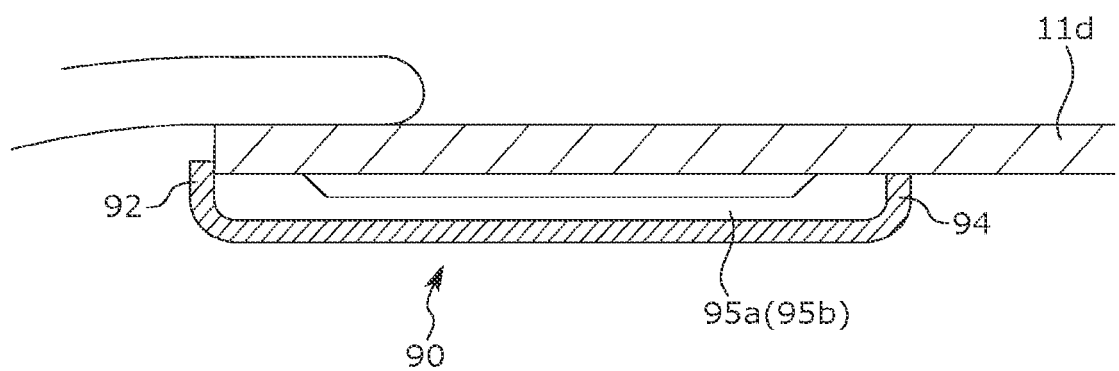
FIG. 12 is an enlarged view of the area around the plate-shaped member of FIG. 3.

In the following, referring to FIGS. 8 to 12, the mounting structure of the awakening unit 60 will be described. FIG. 8 is an illustration of a method of mounting the awakening unit 60 on the lower frame 11*d* of the seat part 11 using the mounting bracket 90. FIGS. 9A and 9B are views showing the mounting bracket 90. FIG. 9A is a perspective view, and FIG. 9B is a front view. FIG. 10 is a view of the awakening unit 60 mounted on the seat part 11 when viewed from above. Note that in FIG. 10, for easily showing the mounting state of the awakening unit 60, the components (specifically, the resin frame 11*a*, the pad material lib, and the skin material 11*c*) located above the lower frame 11*d* of the seat part 11 are not shown. FIG. 11 is a cross-sectional view taken along line A-A in FIG. 10. FIG. 12 is an enlarged view of the area around the mounting bracket 90 in FIG. 3.

First, the configuration of the mounting bracket 90 will be described. The mounting bracket 90 is a plate-shaped member, and has an outside shown in FIGS. 9A and 9B. In the embodiment, the mounting bracket 90 is configured of a metal plate. However, the configuration is non-limiting to this. The mounting bracket 90 may be configured of a resin plate.

The mounting bracket 90 has a nearly rectangular shape when viewed from above. As shown in FIG. 8, the mounting bracket 90 is fixed to the lower frame 11*d* of the seat device 1 with its long side direction being along the width direction of the seat part 11. In specific description, in the center part of the mounting bracket 90 in the long side direction, a fixing hole 93 is formed. The fixing hole 93 corresponds to a plate-shaped member fixing part that is formed to fix the mounting bracket 90 to the seat part 11. Into the fixing hole 93, a bolt that is a fixing component is inserted, and the tip end portion of this bolt is fit into a bolt hole 11*e* formed on the lower frame 11*d*. Thus, the mounting bracket 90 is fixed to the under surface of the lower frame 11*d* (more strictly speaking, the under surface of the front end portion of the lower frame 11*d*).

As shown in FIGS. 8 and 9A, at the two end portions of the mounting bracket 90 in the long side direction, a nail shaped mounting projection 91 is provided. The mounting projection 91 corresponds to a mounting part, and is a portion hanging down in a tongue shape from the edge portion of the end portion of the mounting bracket 90 in the long side direction. As shown in FIG. 8, the mounting projection 91 extends along the vertical direction of the seat part 11 with the mounting bracket 90 fixed to the seat part 11, strictly speaking, the mounting projection 91 protruding downward.

The side wall 80*a* of the holder 80 is mounted on the mounting projection 91. In other words, the side wall 80*a* corresponds to a mounted part mounted on the mounting projection 91. Note that as described later in the embodiment, the side wall 80*a* is mounted on the mounting projection 91 in a predetermined mounting direction.

As shown in FIGS. 8 and 9A, in the embodiment, the mounting projection 91 are provided two each at the two end portions of the mounting bracket 90 in the long side direction. Here, the mounting projection 91 provided at one end portion of the mounting bracket 90 in the long side direction corresponds to a first mounting part, and is referred to as a first mounting projection 91*a* below. The mounting projection 91 provided at the other end portion of the mounting bracket 90 in the long side direction corresponds to a second mounting part, and is referred to as a second mounting projection 91*b* below.

As shown in FIG. 9A, the first mounting projection 91*a* and the second mounting projection 91*b* are formed at positions apart from each other in the long side direction of the mounting bracket 90 (in other words, in the mounting direction, described later). The above-described fixing hole 93 is located between the first mounting projection 91*a* and the second mounting projection 91*b* in the long side direction of the mounting bracket 90 (in other words, in the mounting direction, described later). In other words, the fixing hole 93 is formed between the first mounting projection 91*a* and the second mounting projection 91*b* in the long side direction of the mounting bracket 90. Thus, this enables easy avoidance of the situations of interference with the bolt inserted into the fixing hole 93 to fix the mounting bracket 90 to the seat part 11 in mounting the side wall 80*a* of the holder 80 on the mounting projection 91.

The first mounting projection 91*a* and the second mounting projection 91*b* are provided two each as described above. That is, as shown in FIGS. 9A and 9B, the first mounting projection 91*a* is provided at two positions apart from each other in the short side direction of the mounting bracket 90. Similarly, the second mounting projection 91*b* is also provided at two positions apart from each other in the short side direction of the mounting bracket 90. The mounting projections 91 are individually formed with a through hole 91*h* for screwing.

As shown in FIGS. 8 and 9A, a nail shaped engagement projection 92 is provided at one end portion of the mounting bracket 90 in the short side direction (specifically, the end portion located on the front side with the mounting bracket 90 fixed to the seat part 11). The engagement projection 92 corresponds to an engaging part, and is erected in a tongue shaped from the edge portion of one end portion of the mounting bracket 90 in the short side direction. As shown in FIG. 8, the engagement projection 92 extends along the vertical direction of the seat part 11 with the mounting bracket 90 fixed to the seat part 11, strictly speaking, the engagement projection 92 protruding upward.

As shown in FIG. 10, the engagement projection 92 is engaged with the front end portion of the lower frame 11*d* of the seat part 11 with the mounting bracket 90 fixed to the seat part 11. In other words, the engagement projection 92 is engaged with the lower frame 11*d* as the front to back direction of the seat part 11 (i.e., in the direction intersecting with the mounting direction, described later) is the engaging direction. The engagement projection 92 is thus engaged with the lower frame 11*d*, and hence prevents the mounting bracket 90 from rotating on the lower frame 11*d*. In other words, the engagement projection 92 functions as anti-rotation against the mounting bracket 90. This function more stably fixes the mounting bracket 90 to the lower frame 11*d*.

Note that as shown in FIGS. 8 and 9A, in the embodiment, the engagement projection 92 is formed at two positions apart from each other in the long side direction of the mounting bracket 90 (i.e., in the mounting direction, described later). One engagement projection 92 corresponds to a first engaging part, and is referred to as a first engagement projection 92*a* below. Another engagement projection 92 corresponds to a second engaging part, and is referred to as a second engagement projection 92*b* below.

As shown in FIGS. 8 and 9A, a contact projection 94 in a nail shape is provided at the end portion on the opposite side where the engagement projection 92 is provided in the short side direction of the mounting bracket 90. The contact projection 94 corresponds to a contact part, and is erected in a tongue shaped so as to face the engagement projection 92 in the short side direction of the mounting bracket 90. As shown in FIG. 8, the contact projection 94 extends along the vertical direction of the seat part 11 with the mounting bracket 90 fixed to the seat part 11, strictly speaking, the contact projection 94 protruding upward. The amount of protrusion of the contact projection 94 is smaller than the amount of protrusion of the engagement projection 92 to some extent. In other words, the contact projection 94 is formed such that its top end is lower than the top end of the engagement projection 92.

As shown in FIG. 12, the contact projection 94 is in contact with the under surface of the lower frame 11*d* of the seat part 11 with the mounting bracket 90 fixed to the seat part 11. The contact projection 94 is thus engaged with the under surface of the lower frame 11*d*, and hence the mounting bracket 90 is positioned to the lower frame 11*d*. In other words, the contact projection 94 functions as the positioning of the mounting bracket 90. This function fixes the mounting bracket 90 being positioned at a predetermined fixing position in the vertical direction of the seat part 11.

Note that as shown in FIGS. 8 and 9A, in the embodiment, two contact projections 94 are provided such that the contact projection 94 corresponds to the engagement projection 92. These two contact projections 94 are at positions apart from each other in the long side direction of the mounting bracket 90 (i.e., in the mounting direction, described later). One contact projection 94 corresponds to a first contact part, and is referred to as a first contact projection 94*a* below. Another contact projection 94 corresponds to a second contact part, and is referred to as a second contact projection 94*b* below.

Each of the contact projections 94 is provided at a position corresponding to each of the engagement projections 92 at the end portion of the mounting bracket 90 in the short side direction (at the end portion on the opposite side where the engagement projection 92 is provided). In specific description, the first contact projection 94*a* is provided at the same position at which the first engagement projection 92*a* is provided in the long side direction of the mounting bracket 90. The second contact projection 94*b* is provided at the same position at which the second engagement projection 92*b* is provided in the long side direction of the mounting bracket 90.

As shown in FIGS. 9A and 9B, the mounting bracket 90 is provided with a rib joining the engagement projection 92 to the contact projection 94. In more specific description, between the first engagement projection 92*a* and the first contact projection 94*a*, a first joining rib 95*a* is provided extending so as to join the first engagement projection 92*a* to the first contact projection 94*a*. Between the second engagement projection 92*b* and the second contact projection 94*b*, a second joining rib 95*b* is provided extending so as to join the second engagement projection 92*b* to the second contact projection 94*b*. Both of the first joining rib 95*a* and the second joining rib 95*b* extend along the short side direction of the mounting bracket 90, and their two end portions reach the corresponding engagement projection 92 and the corresponding contact projection 94.

Referring to FIGS. 9A and 9B, the shapes of the first joining rib 95*a* and the second joining rib 95*b* will be described. The midway portions of the upper end surfaces of the joining ribs (the midway portions in the short side direction of the mounting bracket 90) are one step lower than the other parts. Note that the portions other than the midway portions of the upper end surfaces of the ribs are at the same height as the height of the top end of the corresponding contact projection 94, but slightly lower than the top end of the corresponding engagement projection 92. Therefore, in the state in which the mounting bracket 90 is fixed to the seat part 11, in the upper end surfaces of the joining ribs, the portions other than the midway portion that is one step lowered are in contact with the under surface of the lower frame 11*d* of the seat part 11 together with the contact projection 94. Thus, the fixed state of the mounting bracket 90 can be more stabilized. In the mounting bracket 90, the rigidity of the portions fixed to the lower frame 11*d* can be improved.

In this connection, in the embodiment, the under surface of the lower frame 11*d* has a curved surface gently curved in the front to back direction. In other words, in the embodiment, the top ends of the contact projection 94 and the joining ribs are in contact with the under surface of the lower frame 11*d* having the curved surface.

In the embodiment, the first joining rib 95*a* and the second joining rib 95*b* are components separate from the mounting bracket 90, and are mounted on the mounting bracket 90 by welding, for example. However, the configuration is non-limiting to this. A configuration may be provided in which parts corresponding to the first joining rib 95*a* and the second joining rib 95*b* are formed as parts of the mounting bracket 90, and the joining ribs are integrally shaped in shaping the mounting bracket 90. For example, in processing and shaping the mounting bracket 90, a bead (protrusion) may be provided at places where the first joining rib 95a and the second joining rib 95b are provided on the mounting bracket 90, instead of the joining ribs.

Next, a configuration that mounts the awakening unit 60 on the seat part 11 using the above-described mounting bracket 90 will be described. In mounting the awakening unit 60, the vibration imparting device 62, the ECU 70, and the battery 72 are held on the holder 80. After that, the side wall 80a of the holder 80 is mounted on the mounting projection 91 of the mounting bracket 90 (more strictly speaking, the first mounting projection 91a and the second mounting projection 91b) with the mounting bracket 90 fixed to the front end portion of the lower frame 11d of the seat part 11. Thus, the awakening unit 60 is mounted on the seat part 11 through the mounting bracket 90.

As shown in FIG. 8, in the embodiment, the direction in which the side wall 80a of the holder 80 is mounted on the mounting projection 91, i.e., the mounting direction is along the width direction of the seat part 11. In more specific description, the mounting bracket 90 is fixed to the lower frame 11d of the seat part 11 with the long side direction of the mounting bracket 90 being along the width direction of the seat part 11. At the two end portions of the mounting bracket 90 in the long side direction, the mounting projections 91 protruding downward are provided.

As shown in FIG. 8, the holder 80 holding the vibration imparting device 62, the ECU 70, and the battery 72 is brought close to the mounting bracket 90 from below the mounting bracket 90. The holder 80 is then reached at the position at which the mounting bracket 90 is housed in the inside of the side wall 80a. In other words, the mounting bracket 90 is entered into the internal space of the holder 80, and the mounting projections 91 are adjacent to the side wall 80a in the inside of the side wall 80a (strictly speaking, in the side wall 80a, the portion located at the end portion of the seat part 11 in the width direction). In other words, the mounting projections 91 are covered with the side wall 80a from the outer side of the seat part 11 in the width direction.

As shown in FIG. 7, at the portion of the side wall 80a adjacent to the mounting projection 91, a mounting hole 80b is formed. The mounting hole 80b is formed at a plurality of places corresponding to the number of the mounting projections 91 and the positions of the mounting projections 91 (specifically, four places). The mounting holes 80b communicate with the through holes 91h of the corresponding mounting projections 91 (specifically, the mounting projections 91 at the opposite positions). Into both of the mounting hole 80b and the through hole 91h communicating with each other, a tapping screw T that is a mounting component is inserted in the direction along the width direction of the seat part 11. Thus, the side wall 80a of the holder 80 is mounted on the mounting projection 91.

As described above, in the embodiment, the side wall 80a of the holder 80 is mounted on the mounting projections 91, the mounting direction is along the width direction of the seat part 11. With such a configuration, the holder 80 can be more easily mounted on the lower frame 11d of the seat part 11. In more specific description, for example, in the case in which the holder 80 is directly mounted on the lower frame 11d with the tapping screw T, the tapping screw T is to be manipulated along the vertical direction of the seat part 11 (strictly speaking, the tapping screw T is directed upward). In contrast to this, in the embodiment, the tapping screw T is manipulated from the lateral side (i.e., along the width direction of the seat part 11), and hence the manipulation of the screw becomes more easily. Consequently, the awakening unit 60 including the holder 80 is more easily mounted on the lower frame 11d.

In the state in which the side wall 80a of the holder 80 is mounted on the mounting projection 91, the mounting bracket 90 is located in the holder 80. In other words, as shown in FIG. 10, the mounting projection 91 is covered with the side wall 80a of the holder 80 in the width direction of the seat part 11 (i.e., in the mounting direction). As described above, in the embodiment, the side wall 80a eliminates the exposure of the mounting projection 91 with the awakening unit 60 mounted on the seat part 11. Thus, the outside of the seat device 1 including the awakening unit 60 can be made excellent. More specifically, the event that the mounting projection 91 is seen from the lateral side can be avoided.

The front end portion of the seat part 11 has the overhang portion 11t overhanging downward. As shown in FIG. 4, the overhang portion 11t is located on the front side of the front end of the holder 80 with the side wall 80a of the holder 80 mounted on the mounting projection 91. In this state, the overhang portion 11t covers at least a part of the front end of the holder 80 in the front to back direction of the seat part 11. In more specific description, the overhang portion 11t covers the opening reaching the upper portion of the front end of the holder 80. Thus, the front end portion of the holder 80 (specifically, the portion near the opening) is protected by the cover of the overhang portion 11t.

Other Embodiments

The configuration of the seat device according to the present invention is described so far taking an example. However, the above-described embodiment is provided for easily understanding the present invention, and does not limit the present invention. That is, of course, the present invention can be modified and altered without deviating from its gist, and the present invention includes the equivalents of modifications and alterations.

In the foregoing embodiment, the vibration imparting device 62 that improves the wakefulness level of the seated person is used as a moving device. However, the configuration is non-limiting to this. Devices that improve the wakefulness level of the seated person by a stimulus other than vibrations can also be used, such as a device that generates (reproduces) sound, for example. The application of the moving device is not limited to awakening. The moving device may be used for other applications, specifically, the applications that adjust the state of the seated person (e.g. tension level) other than the wakefulness level.

In the foregoing embodiment, the side wall 80a of the holder 80 is mounted on the mounting projection 91 of the mounting bracket 90 with the tapping screw T, and the mounting direction (the screw manipulation direction) is along the width direction of the seat part 11. However, the configuration is non-limiting to this. The mounting direction may be along the front to back direction of the seat part 11. That is, a configuration may be provided in which the mounting projection 91 is provided at the front end or the rear end of the edge portion of the mounting bracket 90 and the tapping screw T is manipulated along the front to back direction of the seat part 11 in mounting the side wall 80a of the holder 80 on the mounting projection 91.

In the foregoing embodiment, the tapping screw T is used as a component that mounts the holder 80 on the mounting bracket 90. However, the configuration is non-limiting to this. A structure may be adopted in which the holder 80 can be mounted on the mounting bracket 90 with a component other than the tapping screw T. For example, a snap-fit structure or a fitting structure using projections and depressions may be adopted. In the case in which such a mounting structure is adopted, the holder 80 may be mounted on the mounting bracket 90 in the vertical direction of the seat part 11.

REFERENCE SIGNS LIST

1: Seat device
10: Chair main body
11: Seat part
   11*a*: Resin frame
   11*b*: Pad material
   11*c*: Skin material
   11*d*: Lower frame (frame)
   11*e*: Bolt hole
   11*f*: Recessed part
   11*t*: Overhang portion (portion overhanging downward)
12: Backrest portion
13: Support post
14: Leg part
20: Respiration sensor unit
21: Pressure sensor (sensor)
22: Conductor wire holding film
   22*a*: Main portion
   22*b*: Branch portion
   22*c*: Wide-width portion
60: Awakening unit
62: Vibration imparting device (moving device)
63: Motor
64: Rotor (moving part)
70: ECU (control mechanism)
71: Termination terminal
72: Battery
80: Holder (Cover)
   80*a*: Side wall (mounted part)
   80*b*: Mounting hole
   80*c*: Concavity part
81: Boss
82: Motor holding part
83: Presser plate
90: Mounting bracket (plate-shaped member)
91: Mounting projection (mounting part)
   91*a*: First mounting projection (first mounting part)
   91*b*: Second mounting projection (second mounting part)
   91*h*: Through hole
92: Engagement projection (engaging part)
   92*a*: First engagement projection (first engaging part)
   92*b*: Second engagement projection (second engaging part)
93: Fixing hole (plate-shaped member fixing part)
94: Contact projection (contact part)
   94*a*: First contact projection (first contact part)
   94*b*: Second contact projection (second contact part)
   95*a*: First joining rib
   95*b*: Second joining rib
T: Tapping screw

The invention claimed is:

1. A seat device comprising:
a seat part on which a seated person is seated;
a vibration imparting device configured to impart vibrations to the seated person; and
a cover configured to cover the vibration imparting device, wherein
the seat part has a frame and a pad material disposed at an upper position of the frame,
the pad material has a recessed part formed on a back side of the pad material,
the vibration imparting device is disposed at a position facing the recessed part in a thickness direction of the pad material,
the cover has a concavity part formed on a front side of the cover, and
the concavity part of the cover is disposed at a position facing the recessed part of the pad material in the thickness direction of the pad material.

2. The seat device of claim 1, wherein the vibration imparting device is disposed at a front position of a front end portion of the frame.

3. The seat device of claim 1, comprising a presser plate configured to cover the vibration imparting device and disposed at an upper position of the cover, wherein
the vibration imparting device is disposed inside the cover and is sandwiched between the concavity part of the cover and the presser plate.

4. The seat device of claim 1, comprising a controller configured to control the operation of the vibration imparting device, wherein
the vibration imparting device is attached to the frame and is disposed at a front position of the controller.

5. The seat device of claim 4, comprising a sensor configured to measure a measurement value relating to a state of the seated person seated on the seat part; and
a termination terminal configured to connect the sensor and the controller, wherein
the termination terminal is disposed at a front position of the controller, and
the vibration imparting device is disposed at a front position of the termination terminal.

6. The seat device of claim 1, wherein
the frame is a lower frame, and
the seat part further has a resin frame disposed at an upper position of the lower frame and at a lower position of the pad material.

7. A method for manufacturing a seat device, wherein the seat device has a seat part on which a seated person is seated, a vibration imparting device configured to impart vibrations to the seated person and a cover configured to cover the vibration imparting device, the seat part has a frame and a pad material, the pad material has a recessed part formed on a back side of the pad material, the cover has a concavity part formed on a front side of the cover, the method comprising:
disposing the pad material at an upper position of the frame,
attaching the vibration imparting device to the seat part so that the vibration imparting device is disposed at a position facing the recessed part of the pad material in a thickness direction of the pad material, and
attaching the cover to the seat part so that the concavity part of the cover is disposed at a position facing the recessed part of the pad material in the thickness direction of the pad material.

8. The method of claim 7, wherein the vibration imparting device is disposed at a front position of a front end portion of the frame.

9. The method of claim 7, wherein the seat device further has a presser plate configured to cover the vibration imparting device and disposed at an upper position of the cover, wherein the vibration imparting device is disposed inside the cover and is sandwiched between the concavity part of the cover and the presser plate.

10. The method of claim 7, wherein the seat device further has a controller configured to control the operation of the vibration imparting device, wherein
the vibration imparting device is attached to the frame and is disposed at a front position of the controller.

11. The method of claim 10, wherein the seat device further has a sensor configured to measure a measurement value relating to a state of the seated person seated on the seat part and a termination terminal configured to connect the sensor and the controller,
the termination terminal is disposed at a front position of the controller, and
the vibration imparting device is disposed at a front position of the termination terminal.

12. The method of claim 7, wherein
the frame is a lower frame, and
the seat part further has a resin frame disposed at an upper position of the lower frame and at a lower position of the pad material.

13. A method for manufacturing a seat device, wherein the seat device has a seat part on which a seated person is seated, a vibration imparting device configured to impart vibrations to the seated person, a controller configured to control the operation of the vibration imparting device, a sensor configured to measure a measurement value relating to a state of the seated person seated on the seat part and a termination terminal configured to connect the sensor and the controller, the seat part has a frame and a pad material, the pad material has a recessed part formed on the pad material, the method comprising:
disposing the pad material at an upper position of the frame,
disposing the termination terminal at a front position of the controller, and
attaching the vibration imparting device to the frame of the seat part so that the vibration imparting device is disposed at a position facing the recessed part in a thickness direction of the pad material and is positioned at a front position of the controller and the termination terminal.

* * * * *